United States Patent [19]
Brandt

[11] Patent Number: 6,076,942
[45] Date of Patent: Jun. 20, 2000

[54] UNIFORMITY FILTER

[75] Inventor: Randolph J. Brandt, Palmdale, Calif.

[73] Assignee: Hughes Electronics Corporation, El Segundo, Calif.

[21] Appl. No.: 09/107,786

[22] Filed: Jun. 30, 1998

[51] Int. Cl.$^7$ .................................................. F21V 21/28
[52] U.S. Cl. ........................................ 362/279; 362/354
[58] Field of Search ............................ 362/355, 358, 362/360, 367, 293, 16, 257, 279, 220, 354; 359/885

[56] References Cited

U.S. PATENT DOCUMENTS

| | | | |
|---|---|---|---|
| 4,099,082 | 7/1978 | Chodil | 313/584 |
| 4,272,804 | 6/1981 | Blum | 362/242 |
| 4,471,596 | 9/1984 | Deaton | 362/354 |
| 5,546,241 | 8/1996 | Mittelman | 359/885 |
| 5,565,742 | 10/1996 | Shichao | 313/257 |
| 5,971,159 | 10/1999 | Leone | 209/399 |

*Primary Examiner*—Sandra O'Shea
*Assistant Examiner*—Hargobind S. Sawhney
*Attorney, Agent, or Firm*—V. D. Duraiswamy; M. W. Sales

[57] ABSTRACT

An apparatus for providing uniform light intensity is disclosed. The apparatus consists of a number of wires arranged diagonally and horizontally on a frame. The horizontal wires are arranged with variable vertical spacing to create eight different zones of light attenuation transmission. The apparatus is designed such that the zones having the highest light attenuation are placed in front of the most intense light from a source and the zones having the lowest light attenuation are placed in front of the least intense light from the source. By matching the zones of the apparatus to the intensity pattern of the light source a uniform light source is created.

31 Claims, 4 Drawing Sheets

UNIFORMITY FILTER

BACKGROUND OF THE INVENTION

(a) Field of the Invention

The present invention relates generally to solar panel testing and, more particularly, to an apparatus for providing uniform light intensity during solar panel testing.

(b) Description of Related Art

Spacecrafts use solar panels to provide electrical power for spacecraft operation and the charging of batteries. A solar panel is made from a number of individual photovoltaic cells, which produce electrical current in response to solar energy. Reliability in the testing of solar panels is very important to both solar panel manufacturing and spacecraft operation.

Currently, solar panel reliability and performance are characterized using a test configuration such as a large area pulse solar simulator (LAPSS). Often there is a fine line between acceptable and unacceptable panels. Therefore, tests used to characterize cell performance must be precise and consistent. Precision and consistency are the keys for determining manufacturing yield and field reliability of the solar panels. Manufacturing yield refers to the number of tested and acceptable solar panels that were produced in a production run of a large number of solar panels. Additionally, correlation and repeatability between test results of different test configurations is desirable. That is, if a particular solar panel fails in a first test configuration, it should also fail in a second test configuration.

Advances in solar panel and solar cell technology have yielded larger and more efficient solar panels. These advances make precision and consistency in product testing even more important because a small difference in light intensity can yield a significant difference in current produced by the solar panel.

A test configuration such as a LAPSS system uses light sources, such as Xenon flash tubes, a series of baffles, and a test bed for measuring the performance of a solar panel. When the light sources illuminate the solar panel, the test bed reads the voltages and currents produced by the panel. A uniform light source is required to prevent cell "hot spots" where light intensity is non-uniformly high and "cold spots" where light intensity is non-uniformly low. Hot spots on the panel occur on the portion of the solar panel that is directly aligned with the light source. Conversely, cold spots occur on the portion of the solar panel that is near the fringe of the light source. Hot spots and cold spots make accurate and repeatable measurements impossible due to the non-uniform illumination of the solar panel. Currently, light sources, such as those used in a LAPSS system, provide reasonably uniform light intensity, but do not take any measures to provide uniform intensity. Additionally, as solar panel sizes and efficiency increase, current test configurations are unable to illuminate the cell with the required light uniformity, thereby magnifying the problems of test reliability and repeatability. Many test configurations require a large panels under test to be moved many times during testing to illuminate sections of the panel with a reasonably uniform light source. The requirement of moving a panel under test limits test accuracy and repeatability, which increases manufacturing cost and time.

The advantages of a highly uniform light intensity device can be readily appreciated. Such a source would increase the reliability and repeatability of test results, thereby accurately predicting the field reliability of solar panels.

SUMMARY OF THE INVENTION

An apparatus for providing uniform light intensity is disclosed. The apparatus consists of a number of wires arranged diagonally and horizontally on a frame. The horizontal wires are arranged with variable vertical spacing to create eight different zones of light attenuation transmission. The apparatus is designed such that the zones having the highest light attenuation are placed in front of the most intense light from a source and the zones having the lowest light attenuation are placed in front of the least intense light from the source. By matching the zones of the apparatus to the intensity pattern of the light source a uniform light source is created.

The present invention is an apparatus for providing uniform light intensity. The apparatus includes a light source, and a light baffle having a uniformity filter disposed within the opening of the baffle. The uniformity filter is constructed from three sets of wires. The first and second sets of wires are mounted to a filter frame at forty five and one hundred thirty five degrees with respect to the horizontal. The third set of wires is disposed substantially parallel to the horizontal. The spacing between the wires of the third set is used to create a number of light attenuation zones that attenuate optical energy to different degrees, thereby making the light source appear uniform in intensity. As the wires transition between the zones of the uniformity filter, certain of the wires will be terminated at the interface between zones. The remaining wires are distributed within the next zone and are spaced regularly at the interface between the next zone and a subsequent zone.

The invention itself, together with further objects and attendant advantages, will best be understood by reference to the following detailed description, taken in conjunction with the accompanying drawings.

DESCRIPTION OF THE PREFERRED EMBODIMENTS

The present invention is an apparatus for delivering uniform light intensity to a solar panel under test. Uniform light intensity increases the reliability and accuracy of tests performed on a solar panel. The present invention is intended as an addition to existing systems in the field or as a feature for sale with new test systems. The present invention is a uniformity filter having eight different zones that allow the passage of light from a flash lamp in varying degrees to provide light having a uniform intensity onto a surface. The various zones of the filter are created by arranging horizontal wires with various vertical spacing. Since "hot spots" are likely to form in the center of the light pattern, wires near the center of the filter are arranged closest together for maximum light attenuation. Conversely, wires near the edges of the filter are spaced farther apart to minimize light attenuation. The theory of operation of the present invention is that the filter attenuates all light passing through the filter to some degree so that the intensity of the light passing through the edges of the filter is approximately the same as the light passing through the center of the filter.

Figure 1:
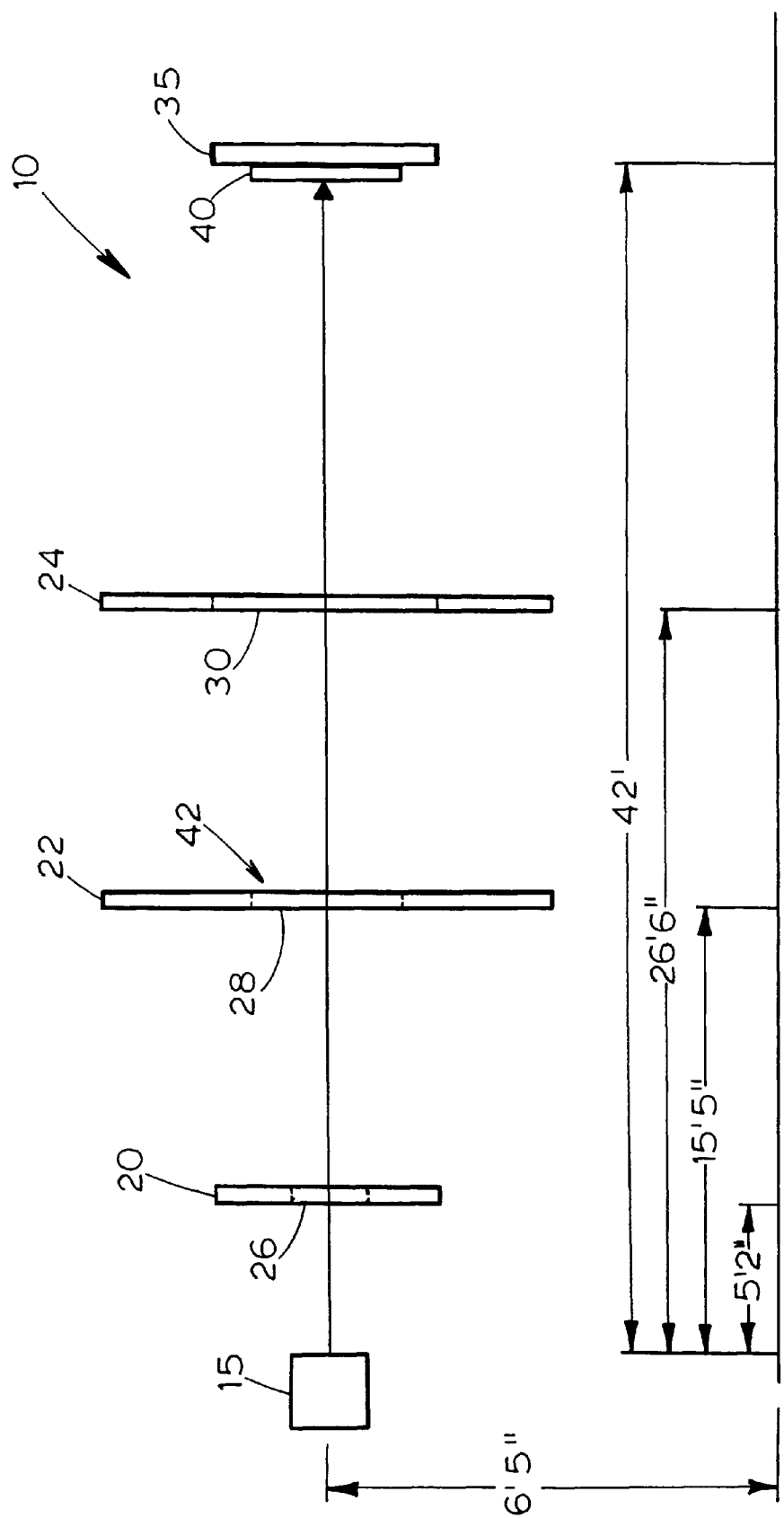
FIG. 1 is an illustration of a solar panel test system that may employ the uniformity filter of the present invention.

FIG. 1 is an illustration of a test system 10 that may employ the present invention. The test system 10 includes a flash lamp 15, a series of light baffles 20, 22, 24 having apertures 26, 28, 30 to allow light from the flash lamp 15 to pass to a test bed 35 holding a solar panel under test 40. As the solar panel under test 40 is illuminated by the flash lamp 15, the outputs of the solar panel under test 40 are measured. A uniformity filter of the present invention 42 is installed in the aperture 28 of the second baffle 22. The size of the filter 42 and the aperture 28 of the second baffle 22 is preferably six feet by six feet square in this embodiment.

Filters and apertures of other physical dimensions and forms may be used. For example, it is possible to provide the baffles 20, 22, 24 with circular apertures and design a circular filter to fit within one of the apertures. Additionally, a test system may use more or fewer baffles than disclosed. Moreover, the uniformity filter of the present invention may be disposed in the aperture of any one of the baffles of the test system.

Figure 2:
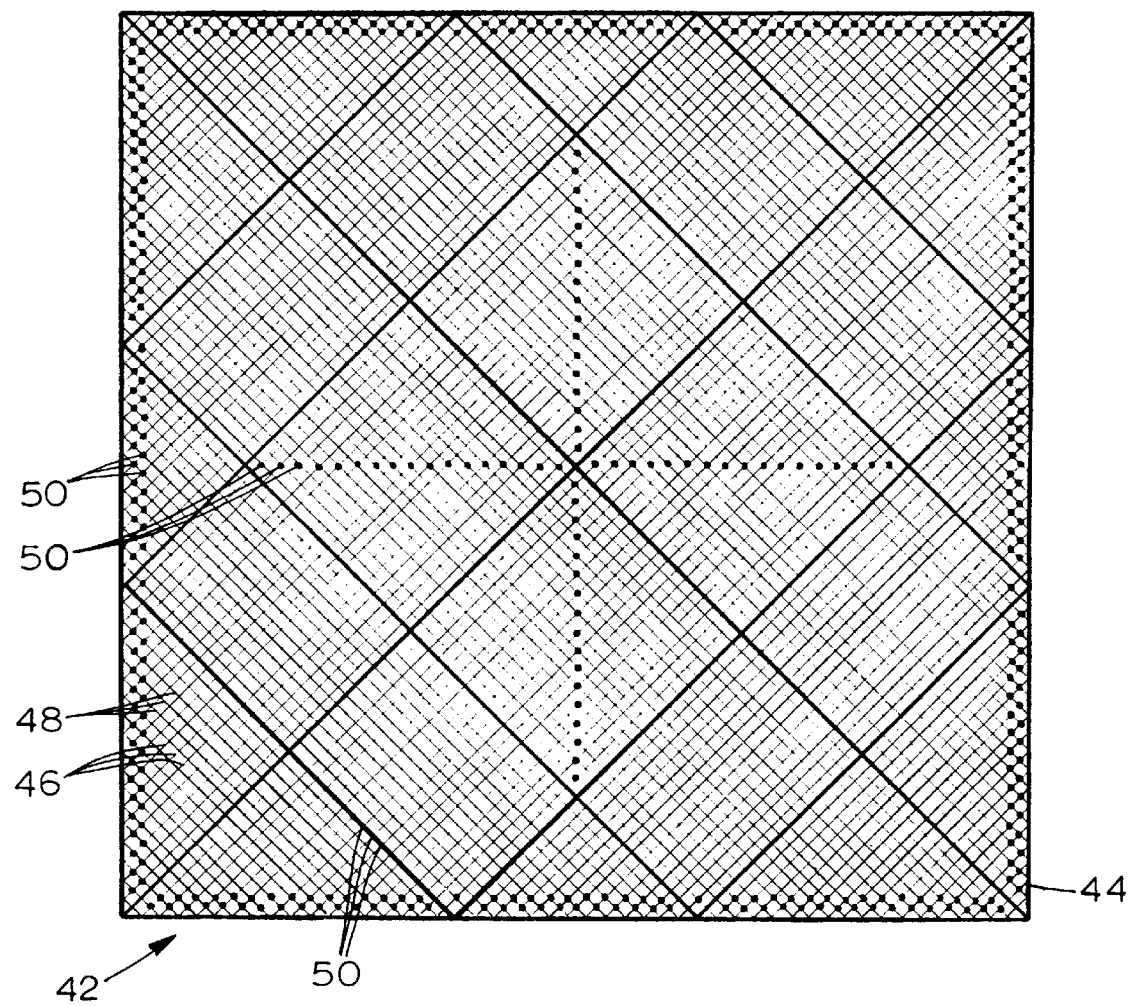
FIG. 2 is an illustration of a base of the uniformity filter of the present invention.

The uniformity filter 42 of the present invention is constructed using a two-step process. The first step is the construction of a base having uniform light passing characteristics. FIG. 2 is an illustration of a base 43 that includes a frame 44, a first set of wires 46 arranged in a first direction, a second set of wires 48 arranged in a second direction. Preferably, the sets of wires 46, 48 are disposed diagonally on the frame 44 and the angle between the sets of wires is 90°. It is also preferable that the wires in each set 46, 48 are disposed one inch on center.

The frame 44 on which the sets of wires 46, 48 are mounted is preferably constructed of one inch square aluminum tubing, each side of the frame having a length of six feet. After the frame has been assembled, preferably forty-nine equally-spaced rivets are disposed along the inside center of each side of the frame. Two 0.010" diameter nickel wires 46, 48 are attached to each rivet. The wires 46, 48 form 45° and 135° angles, respectively, with respect to the bottom horizontal member of the frame. For example, wires are connected from the bottom left corner of the frame to the top right of the frame. Likewise, wires are connected from the bottom right corner to the top left corner. This process is repeated until two wires at right angles to one another are connected to each rivet. It should be understood that a number of alternate fasteners may be used in place of rivets. Furthermore an alternate number of fasteners may be selected for use other that forty-nine. Moreover, the number, the thicknesses, and compositions of the wires may be used in the construction of the base 43.

After all diagonal wires 46, 48 have been placed, the intersecting wires 46, 48 are bonded together at solder joints 50 to increase base stability. The wires 46, 48 are soldered in a pattern as shown in FIG. 2, where the bold lines and the dotted lines indicate solder joints. That is, the intersecting wires 46, 48 are soldered together in a diamond pattern and a vertical cross pattern as shown in FIG. 2. Additionally, the intersecting wires 46, 48 are soldered in accordance with the dotted pattern shown along the edge of the frame.

Figure 3:
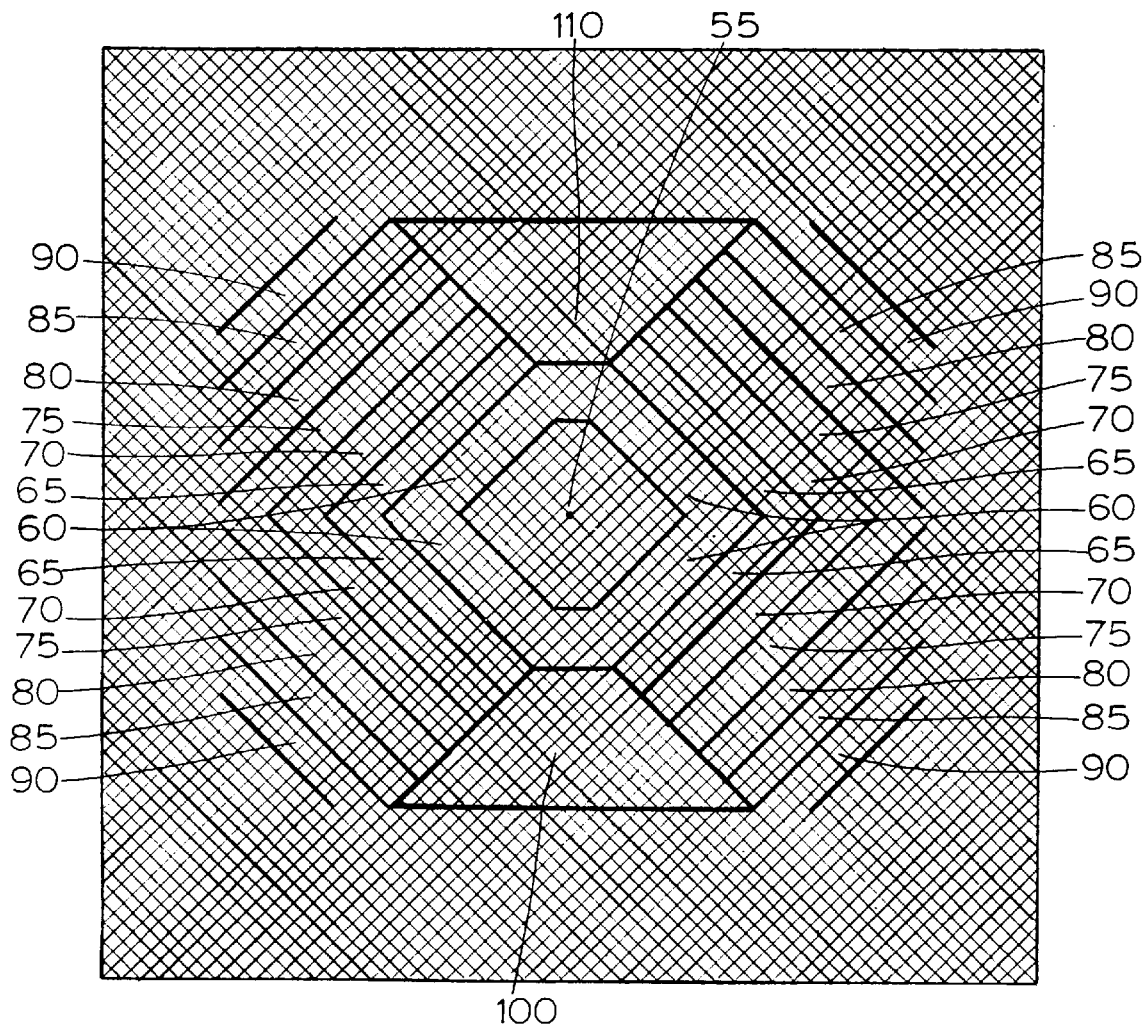
FIG. 3 is an illustration of the uniformity filter of the present invention.

After the filter base 43 is complete, horizontal wires (e.g., the wires 115, 120 and 125 shown in FIG. 4) are installed with eight different spacings to create eight different levels of light attenuation. FIG. 3 represents the eight different levels of attenuation of the filter 42. Each section (or zone) corresponds to a particular spacing of horizontal wires and a particular level of light intensity attenuation. The required wire spacing and attenuation of light intensity are shown in Table 1 for sections (or zones) 55–90.

TABLE 1

| Section | Vertical Wire Spacing | Light Intensity Attenuation |
|---|---|---|
| 55 | 0.25" | 4.5% |
| 60 | 0.28" | 4.0% |
| 65 | 0.33" | 3.5% |
| 70 | 0.39" | 3.0% |
| 75 | 0.48" | 2.5% |
| 80 | 0.62" | 2.0% |
| 85 | 0.88" | 1.5% |
| 90 | 1.50" | 1.0% |

As shown in Table 1, the center of the filter 42 (i.e., section 55) has the highest density of horizontal wires. As wires from section 55 reach the section 60 and subsequent sections, some wires will be terminated and not used in the sections having lower wire density, with the remaining horizontal wires redistributed with the required spacing.

Figure 4:
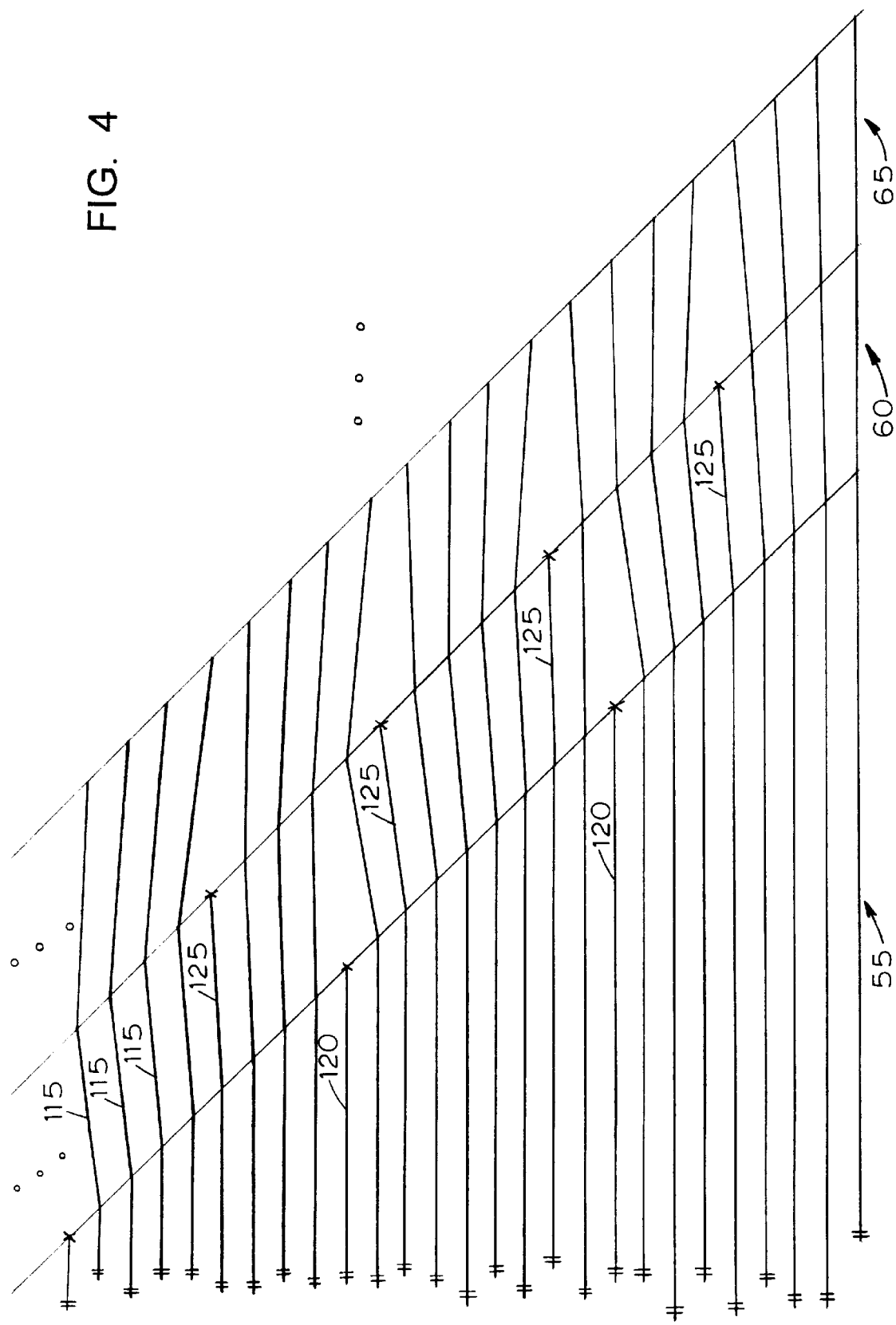
FIG. 4 is a detailed schematic of the horizontal wire spacing transitions used in the uniformity filter of the present invention.

FIG. 4 is a detailed illustration of a wire spacing transitions showing a portion of three sections 55, 60, 65 of the filter 42 and the wire spacing and transitions. In a five inch vertical portion of section 55, there will be 21 wires spaced 0.25" on center. Five inch vertical portions of sections 60 and 65 will have 19 wires spaced at 0.28" and 15 wires spaced at 0.33", respectively. Certain wires 115 extend across all sections 55, 60, 65 shown, other wires 120, 125 will terminate at interfaces between sections. As the wires from section 55 reach the boundary of section 60 certain wires 120 will be terminated. In the section shown in FIG. 4, every ninth wire 120 from section 55 will be terminated at the boundary between sections 55 and 60. Likewise, every fifth wire 125 from section 60 will be terminated at the boundary between sections 60 and 65. As the wires are connected from the boundary of sections 55 and 60 to the boundary of sections 60 and 65 the spacing of the wires transitions from an irregular spacing to a regular spacing of 0.28". Because of the change in the number of wires from section to section, some of the wires will be sloped with respect to the horizontal as the wires transition from one section to another. However, because of the relatively large horizontal distances that the wires cover, the slope of the wires as they transition from one spacing to the next is typically only a few degrees from horizontal. This method of eliminating certain wires is duplicated for each transition between sections.

Referring back to FIG. 3, sections 100 and 110 also have wires distributed horizontally within them. The spacing and quantity of wires used is shown in Table 2.

TABLE 2

| Quantity | Spacing |
|---|---|
| 5 | 0.28" |
| 7 | 0.33" |
| 6 | 0.39" |
| 5 | 0.48" |
| 3 | 0.62" |
| 3 | 0.88" |
| 2 | 1.50" |

The closely spaced wires are installed at the top of section 100 and at the bottom of section 110. The wire spacing is closest near the center of the filter and increases near the edges of the filter. Configured in this way, the maximum wire density, and therefore the maximum light attenuation, is located at the center of the filter 42 where light intensity from the flash lamp 15 is the strongest.

After the horizontal wires have been properly installed, the filter 42 is preferably painted with a gray primer (to eliminate light reflections) and installed into the aperature 28 of the second baffle 22 as shown in FIG. 1.

Although the preferred embodiment of the present invention uses wires that are substantially horizontal, it should be noted that alternative wire configurations may be used. For example, wire configurations such as vertically disposed wires, concentrically disposed wires or radially disposed may be used. Of course, it should be understood that a range of changes and modifications can be made to the preferred embodiment described above. For example, the wire may be disposed on the frame in configurations such as, circular, elliptical or other configurations different from the preferred embodiment, as long as the pattern of wires used attenuates light in different zones that correspond to the intensity pattern of a light source. Additionally, other wire diameters may be used and the wire used may be made from metal other than nickel. It is therefore intended that the foregoing detailed description be regarded as illustrative rather than limiting and that it be understood that it is the following claims, including all equivalents, which are intended to define the scope of this invention.

What is claimed is:

1. An apparatus for providing uniform light intensity, said apparatus comprising:
   a light source;
   a light baffle, said baffle comprising an opening for passing light; and
   a uniformity filter disposed in said opening of said light baffle, said uniformity filter comprising a plurality of zones that attenuate light to various degrees, wherein each of said plurality of zones comprises a plurality of wires.

2. The apparatus of claim 1, wherein said light source is projected through said baffle.

3. The apparatus of claim 1, wherein said uniformity filter comprises:
   a frame comprising left and right vertical sides and top and bottom horizontal sides, wherein the plurality of wires are connected to the frame.

4. The apparatus of claim 3, wherein said plurality of wires comprises:
   a first set of wires arranged in a first orientation on said frame;
   a second set of wires arranged in a second orientation on said frame; and
   a third set of wires configured in a third orientation on said frame.

5. The apparatus of claim 4, wherein said first set of wires is oriented on said frame at approximately forty-five degrees with respect to said bottom horizontal side of said frame.

6. The apparatus of claim 4, wherein said second set of wires is oriented on said frame at approximately ninety degrees with respect to said first set of wires.

7. The apparatus of claim 4, wherein said third set of wires is oriented on said frame substantially parallel to said bottom horizontal side of said frame.

8. The apparatus of claim 7, wherein said third set of wires comprises a plurality of substantially horizontal wires distributed at vertical distances to create said plurality of zones.

9. The apparatus of claim 8, wherein said vertical distances between said wires varies proportionately with a distance from the center of said frame.

10. The apparatus of claim 8, wherein said vertical distances are inversely proportional to an amount of light intensity attenuation.

11. The apparatus of claim 10, wherein each of said zones has said wires distributed at unique vertical distances.

12. The apparatus of claim 11, wherein said wires at a boundary between a first zone and a second zone have a first distance of separation.

13. The apparatus of claim 12, wherein said wires at a boundary between a second zone and a third zone have a second distance of separation greater than said first distance of separation.

14. The apparatus of claim 13, wherein a number of wires from said first zone are terminated at said boundary between said first zone and said second zone, a remaining number of wires being distributed within said second zone.

15. The apparatus of claim 14, wherein said remaining wires are evenly spaced at said boundary between said second zone and said third zone.

16. An apparatus for providing uniform light intensity, said apparatus comprising:
   a frame comprising left and right vertical sides and top and bottom horizontal sides; and
   a plurality of zones that attenuate light to various degrees, wherein each of said plurality of zones comprises a plurality of wires.

17. The apparatus of claim 16, wherein each of said plurality of wires comprises:
   a first set of wires arranged in a first orientation on said frame;
   a second set of wires arranged in a second orientation on said frame; and
   a third set of wires configured in a third orientation on said frame.

18. The apparatus of claim 17, wherein said first set of wires is oriented on said frame at approximately forty-five degrees with respect to said bottom horizontal side of said frame.

19. The apparatus of claim 17, wherein said second set of wires is oriented at approximately ninety degrees with respect to said first set of wires.

20. The apparatus of claim 17, wherein said third set of wires is oriented on said frame substantially parallel to said bottom horizontal side of said frame.

21. The apparatus of claim 20, wherein said third set of wires comprises a plurality of substantially horizontal wires distributed at vertical distances to create said plurality of zones.

22. The apparatus of claim 21, wherein said vertical distances are inversely proportional to an amount of light intensity attenuation.

23. The apparatus of claim 22, wherein each of said zones has said wires distributed at unique vertical distances.

24. The apparatus of claim 23, wherein said wires at a boundary between a first zone and a second zone have a first distance of separation.

25. The apparatus of claim 24, wherein said wires at a boundary between a second zone and a third zone have a second distance of separation greater than said first distance of separation.

26. The apparatus of claim 25, wherein a number of wires from said first zone are terminated at said boundary between said first zone and said second zone, a remaining number of wires being distributed within said second zone.

27. The apparatus of claim 26, wherein said remaining wires are evenly spaced at said boundary between said second zone and said third zone.

28. A method of constructing a filter for making a uniform illumination pattern from a non-uniform light source, the steps comprising:
 providing a frame;
 arranging a first set of wires on said frame with first orientation;
 arranging a second set of wires on said frame with second orientation;
 arranging a third set of wires on said frame with third orientation, wherein said first, second and third sets of wires form a plurality of zones that attenuate light to various degrees.

29. The method of claim 28, wherein said second set of wires is orientated at approximately ninety degrees with respect to said first set of wires.

30. The method of claim 28, wherein said third set of wires is arranged horizontally having a vertical spacing between said horizontal wires.

31. The method of claim 30 wherein, said vertical spacing of said third set of wires is proportional to a distance from the center of said frame.

* * * * *